United States Patent [19] [11] 4,303,788
Durden, Jr. et al. [45] Dec. 1, 1981

[54] 2-OXIMINO-TETRAHYDRO-1,4-OXAZIN-3-ONES

[75] Inventors: John A. Durden, Jr., South Charleston; Arthur P. Kurtz, Jr., Charleston, both of W. Va.

[73] Assignee: Union Carbide Corporation, New York, N.Y.

[21] Appl. No.: 148,511

[22] Filed: May 9, 1980

Related U.S. Application Data

[62] Division of Ser. No. 698,029, Jun. 21, 1976, Pat. No. 4,235,902.

[51] Int. Cl.$^3$ .................. A01N 43/84; C07D 265/32; A01N 43/78
[52] U.S. Cl. ...................................... 544/164; 424/272
[58] Field of Search ......................................... 544/164

[56] References Cited

U.S. PATENT DOCUMENTS 3,843,669 10/1974 Punja ..................................... 424/272
4,235,902 11/1980 Duren, Jr. et al. ................. 544/164

*Primary Examiner*—Anton H. Sutto
*Attorney, Agent, or Firm*—Clement J. Vicari; William R. Moran

[57] ABSTRACT

Certain 2-oximino-tetrahydro-1,4-oxazin-3-one and 5-oximino-1,3-oxazolidin-4-one carbamate esters exhibit outstanding miticidal, insecticidal and nematodicial activity; certain 2-oximino-tetrahydro-1,4-oxazin-3-ones and 5-oximino-1,3-oxazolidin-4-ones are useful intermediates in the preparation of pesticidally active carbamate compounds.

6 Claims, No Drawings

2-OXIMINO-TETRAHYDRO-1,4-OXAZIN-3-ONES

This is a division of our prior U.S. application Ser. No. 698,029 filed June 21, 1976, and now U.S. Pat. No. 4,235,902.

This invention relates to a novel class of compounds and to their preparation.

More particularly, this invention relates to a novel class of compounds of the formula:

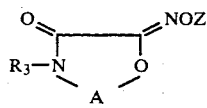

wherein

Z is hydrogen or

wherein:

$R_1$ and $R_1$ are:

(a) individually hydrogen, alkyl, alkenyl or alkynyl; or (b) when $R_1$ is alkyl, $R_2$ may also be alkanoyl, trihalomethanesulfenyl, alkylsulfenyl, alkylthiosulfenyl, cycloalkylsulfenyl, cycloalkylthiosulfenyl, or substituted or unsubstituted phenylsulfenyl or phenylthiosulfenyl wherein the permissible substituents are one or more chloro, bromo, fluoro, nitro, cyano, alkoxy or alkyl substituents in any combination;

$R_3$ is hydrogen, alkyl, cycloalkyl, alkoxyalkyl or phenyl;

A is methylene or ethylene either unsubstituted or substituted with one or more alkyl;

Alkyl, alkanoyl, alkynyl, cycloalkyl, alkoxyalkyl and alkenyl moieties individually may not include more than 6 carbons.

Preferred because of their higher level of pesticidal activity are the compounds of this invention wherein:

Z is hydrogen or

wherein:

$R_1$ and $R_2$ are:

(a) individually hydrogen or alkyl; or (b) when $R_1$ is alkyl, $R_2$ may be alkanoyl or trihalomethanesulfenyl;

$R_3$ is hydrogen or alkyl;

A is ethylene either unsubstituted or substituted with one or more alkyl substituents; wherein alkyl or alkanoyl substituents individually may include from 1 to 4 carbons.

The carbamate compounds of this invention are those wherein Z is

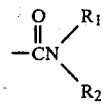

and $R_1$, $R_2$, $R_3$ and A are as described above. These compounds exhibit outstanding insecticidal activity against such major economic pests as aphid, house fly, Southern armyworm and Mexican Bean Beetle. Certain of these compounds also exhibit excellent nematocidal and miticidal activity. They are also relatively non-toxic to plants and mammals when used in amounts sufficient to kill insects, nematodes and mites.

This invention also relates to nematocidal, insecticidal and miticidal compositions comprising an acceptable carrier and a nematocidally, insecticidally or miticidally effective amount of a carbamate compound of this invention. This invention also includes a method of controlling insects, nematodes and mites by subjecting them to an insecticidally, nematocidally or miticidally effective amount of a heterocyclic carbamate compound of this invention.

The oxime compounds of this invention are those wherein Z of the above formula is hydrogen and $R_3$ and A are as described above. These compounds are useful as intermediates in the preparation of insecticidally, nematocidally and miticidally active heterocyclic carbamate compounds. For example, 2-oximino-4-methyl-tetrahydro-1,4-oxazin-3-one can be reacted with an appropriately substituted carbamoyl halide as for example, N-methyl-N-trichloromethanesulfenylcarbamoyl fluoride, in the presence of an acid acceptor such as triethylamine to produce 2-[N-trichloromethanesulfenyl-N-methylcarbamoyloximino]-4-methyltetrahydro-1,4-oxazin-3-one, the corresponding pesticidally active heterocyclic carbamate compound. The oxime compounds of this invention can also be reacted with other chemical species containing electron deficient reaction sites, such as isocyanates or phosgene followed by appropriate amines to prepare pesticidally active heterocyclic carbamate compounds. These reactions are disclosed in more detail below.

The carbamate compounds of this invention can be conveniently prepared employing a variety of methods which utilize the oxime compounds of this invention as precursors. One method for producing the carbamate compounds of this invention is by reacting the corresponding oxime with a carbonyl halide in the presence of an acid acceptor to form the haloformate which is then aminolyzed by reaction with an appropriately substituted amine as illustrated in the following general reaction scheme:

METHOD I

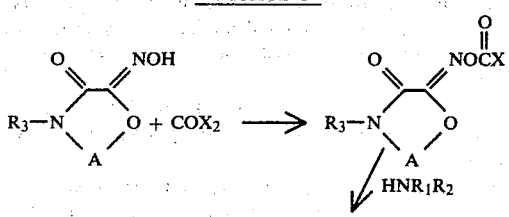

-continued
METHOD I

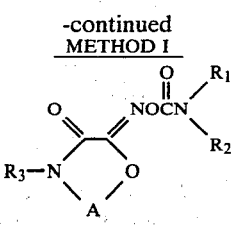

In the above reaction scheme $R_3$ and A are as described above. $R_1$ and $R_2$ are individually hydrogen, alkyl, alkenyl or alkynyl and X is chlorine or fluorine.

Heterocyclic carbamate compounds according to this invention wherein $R_2$ is hydrogen can be prepared by reacting the corresponding oxime with an appropriately substituted isocyanate in the presence of a suitable catalyst as shown in the following general reaction scheme:

METHOD II

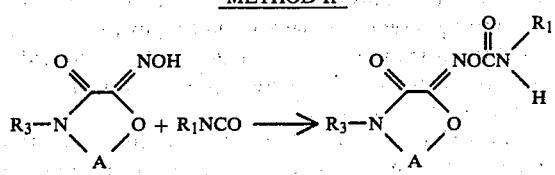

In the above reaction scheme $R_3$ and A are as described above and $R_1$ is alkyl, alkynyl or alkenyl.

The carbamates of this invention can also be prepared by reacting the corresponding oxime with an appropriately substituted carbamoyl halide in the presence of a acid acceptor as illustrated in the following general reaction scheme:

METHOD III

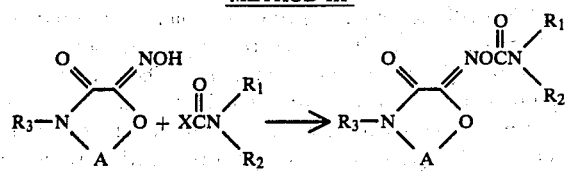

in which $R_1$, $R_2$, $R_3$ and A are as defined above and X is chlorine or fluorine.

These reactions are conducted under very similar reaction conditions. Substantially equimolar amounts of the reactants are contacted in an inert solvent. Any inert solvent can be used such as benzene, toluene xylene, dioxane, tetrahydrofuran, ethyl ether, methylene chloride or the like.

The reactions can be conducted in a heterogeneous phase system or a homogenous phase system. In the former case, phase transfer agents, such as crown ethers and quaternary ammonium halides may be used to facilitate the transfer of reactants across the phase interface.

Reaction temperatures are not critical and may vary widely depending to a large extent on the stability and reactivity of the reagents. Usually, the reaction is conducted at a temperature of from about $-10°$ C. to about $80°$ C.

Reaction pressures are not critical. For convenience the reaction is conducted at atmospheric or autogenous pressure.

The reactions illustrated in Methods I and III are conducted in the presence of an acid acceptor. The acid acceptor employed is a basic material which can be either an organic or an inorganic base. Suitable inorganic bases include alkali metal hydroxides such as sodium hydroxide, potassium hydroxide or the like. Organic bases which are useful include organic amines, alkali metal alkoxides or the like. Preferred acid acceptors are tertiary amines, such as pyridine, triethylamine, 1,4-diazabicyclo [2.2.2] octane or the like. In general, the molar ratio of acid acceptor to either reactant is substantially equimolar or a slight excess.

The reaction illustrated in Method II is preferably conducted in a presence of a catalyst. Any conventional catalyst of the type commonly employed to promote reactions between isocyanate compounds and compounds containing an active hydrogen can be used. Preferred catalyst are tertiary amines such as pyridine, triethylamine or the like. Generally, the reaction is conducted in the presence of a quantity of catalyst sufficient to provide a suitable and reasonable reaction rate.

Carbamoyl halide precursors can be prepared in accordance with a variety of conventional methods. N-thiosulfenylated and N-sulfenylated carbamoyl fluorides can be prepared by reacting hydrogen fluoride with an appropriately substituted isocyanate to form the mono-substituted carbamoyl fluoride which is then reacted with an appropriately substituted thiosulfenyl or sulfenyl N-thiosulfenylated or N-sulfenylated compound respectively. For example, methyl isocyanate can be reacted with hydrogen fluoride in toluene to form N-methyl carbamoyl fluoride which, in turn, can be reacted in situ with p-tert-butylphenylthiosulfenyl chloride in the presence of triethylamine to form N-methyl-N-(p-tert-butylphenylthiosulfenyl) carbamoyl fluoride.

The preparation of N-sulfenylated carbamoyl halides is described in more detail in U.S. Pat. No. 3,639,471.

The remaining carbamoyl halide percursors, in which $R_1$ and/or $R_2$ are bonded to nitrogen through a carbon nitrogen bond can be prepared by reacting an appropriately substituted amine with a carbonyl halide, such as phosgene.

The heterocyclic oxime precursors, which are novel compounds according to this invention are prepared by reacting a corresponding heterocyclic lactam with an acid acceptor and a nitrite ester followed by neutralization with acid as illustrated in the following reaction scheme:

METHOD IV

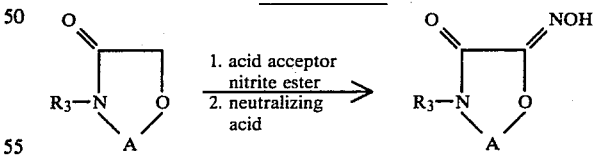

wherein $R_3$ and A are as described above.

The reaction is preferably carried out in an inert solvent. Any inert solvent can be used such as benzene, toluene, xylene, dioxane, tetrahydrofuran, dimethoxyethane, ethyl ether, methylene chloride or the like.

Illustrative of nitrile esters which are useful are alkyl nitrite esters such as ethyl nitrite, isobutyl nitrite or the like.

The acid acceptor employed can be either a strong organic or a strong inorganic base. Suitable organic bases include alkali metal alkoxides, alkylides and the like, and suitable inorganic bases include alkali metal hydroxides or the like. Alkali metal alkoxides of low nucleophilicity are preferred acid acceptors.

The reaction can be conducted in either a homogenous phase system or heterogeneous phase system. In the latter case phase transfer agents, such as a crown ether or a quaternary ammonium halide, can be used to facilitate the transfer of reactants across the phase interface.

After the reaction has gone to completion, usually in from about 0.5 hr. to about 20 hours, the oxime salt is neutralized by the addition of an organic or inorganic acid, such as hydrochloric acid, acetic acid or the like.

Reaction temperatures are not critical and may be varied widely depending to a large extent on the stability and reactivity of the reactants. Usually, the reaction is conducted at a temperature of from about $-70°$ C. to about $100°$ C. Reaction pressures are not critical, but usually the reaction is conducted at atmospheric or autogenous pressure.

Heterocyclic lactam precursors used in the preparation of the oxime compounds of this invention can be prepared by reacting an appropriate substituted alkanol amine with sodium metal to form the corresponding sodium alkanolate salt which, in turn, is reacted usually in situ with an alkyl alpha-haloalkanoate to achieve cyclization. This procedure is disclosed in more detail in Example I below. Compounds in which $R_3$ is hydrogen are readily convertible into the corresponding N-substituted derivatives via well known conventional methods including but not limited to; alkylation methods, utilizing reagents such as alkali metal hydroxides and an alkyl halide.

EXAMPLE I

Preparation of 4-Ethyltetrahydro-1,4-oxazin-3-one

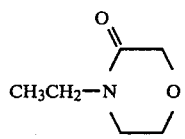

The Example I compound was prepared according to the following modification of the procedure of P. Vieles and J. Sequin (*Compt. rend.* 234, 1980 [1952]). A solution of sodium 2-ethylaminoethylate was prepared from 178.0 grams of 2-ethylaminoethanol and 46.0 grams of sodium in 1500 ml of tetrahydrofuran. To this solution was added 246 grams of ethyl chloroacetate over approximately 10 minutes while maintaining the temperature at $-10°$ to $-20°$ during the addition by means of external cooling. After one hour at $-20°$, the reaction mixture was allowed to warm to ambient temperatures for two hours and then stirred at $70°$ for 18 hours. The mixture was then cooled to $25°$ and residual basicity neutralized by addition of 30 ml of conc. hydrochloric acid. Sodium chloride was then removed by filtration and the filtrate was vacuum concentrated and distilled to yield 167.3 grams of the product, bp. $75°-78°/0.01$ mm. Carbonyl infrared absorption at $6.05\mu$ and the absence of bands in the carbonyl region at wavelengths below $6.0\mu$ confirmed lactam rather than lactone ring formation. NMR (Acetone, $\delta$): 1.08, triplet, $CH_3$; 3.88, Quartet, $CH_2(CH_3)$; 3.98, singlet, $CH_2(CO)$; 3.33, triplet, $NCH_2(CH_2O)$; 3.84, triplet, $OCH_2(CH_2N)$.

Anal. Calc'd for $C_6H_{11}NO_2$: C, 55.80; H, 8.58; N, 10.84; Found: C, 54.84; H, 8.18; N, 10.57.

EXAMPLE II

Preparation of 4-Methyl-5-ethyltetrahydro-1,4-oxazine-3-one

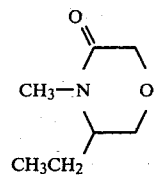

A solution of the crude intermediate 4-methyl-5-ethyl-tetrahydro-1,4-oxazine-3-one was prepared in a manner similar to that described in Example I by reacting the sodium salt of 2-amino-butan-1-ol (from 240 g of the amino alcohol and 62 grams of sodium) in 2500 ml of tetrahydrofuran with 338 g of ethyl chloroacetate following alcohol and 62 grams of sodium) in 2500 ml of evaporation of the reaction solvent, the crude product was taken up in chloroform and washed with water. After drying the organic solution and removal of the solvent, recrystallization of the crude product from isopropyl ether/ethyl acetate yielded 151 grams of 5-ethyl-tetrahydro-1,4-oxazin-3-one, m.p. $70°-73°$. Absence of carbonyl absorption bands in the infrared in the lactone region and the presence of a strong band at $6.10\mu$ confirmed lactam rather than lactone cyclisation. Other major IR bands: 3.42, 3.52, 6.7, 6.8, 7.0, 7.2, 7.5, 7.8, 8.0, 8.7, 8.9, 8.98, 9.2, 9.5, 10.1, 10.5, 10.9, 11.8, 12.4 and $13.8\mu$ NMR($CDCl_3$, $\delta$): 2.95, singlet, $NCH_3$; 3.2, multiplet, $N-CH(CH_2CH_3)$; 1.75, quintet, $CH_2(CH_3)$; 0.93 triplet, $CH_3(CH_2)$; 3.78 and 3.84, AB pair, $CH_2O$; 4.07 singlet, $CH_2CO$.

Methylation of the secondary lactone by reaction with one equivalent of sodium hydroxide and excess methyl iodide in dimethoxyethane afforded, after conventional workup and vacuum distillation, 55 grams of 4-methyl-5-ethyltetrahydro-1,4-oxazin-3-one, by $68°-72°/0.10$ mm.

Anal: Calc'd for $C_7H_{13}NO_2$: C, 55.79; H, 8.58; N, 10.84; Found: C, 54.43; H, 8.05; N, 10.53.

EXAMPLE III

Preparation of 2-Oximino-4-methyltetrahydro-1,4-oxazin-3-one

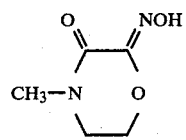

While maintaining the temperature near $-55°$, a solution of 11.5 grams of 4-methyltetrahydro-1,4-oxazin-3-one dissolved in 100 ml of anhydrous tetrahydrofuran was added over a period of twenty minutes to a slurry of 14.6 grams of potassium t-butoxide in 100 ml of tetrahydrofuran vigorously stirring under a nitrogen atmosphere. After equilibrating the resultant mixture for 30 minutes at $-60°$, a solution of 11.4 grams of isobutyl nitrite in 50 ml of tetrahydrofuran was added over 15 minutes while maintaining the temperature at $-60°$ with external cooling. After a 15-minute equilibration at $-60°$, the reaction mixture was brought to $25°$ and stirred for 3 hours. The solution was then cooled to $0°$ and neutralized to pH 5 with 65 ml of a solution of 18 ml of conc. hydrochloric acid diluted to 100 mls. with absolute ethanol. After a 15-minute equilibration, potassium chloride was filtered off and the solvent removed in vacuuo. The resulting oil was triturated with 50 ml of ethyl acetate and the resulting solid was collected and then recrystallized from 150 ml. of acetonitrile yielding 5.07 g of the oxime product, mp. 199°–201°.

Anal: Calc'd for $C_5H_8N_2O_3$: C, 41.67; H, 5.59; N, 19.43; Found: C, 41.17; H, 5.49; N, 1920.

EXAMPLE IV

Preparation of 2-Oximino-4-methyl-5-ethyltetrahydro-1,4-oxazin-3-one

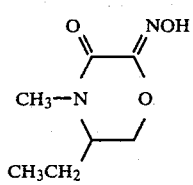

A quantity of 33.7 g of potassium t-butoxide, 40.0 g of 4-methyl-5-ethyl-tetrahydro-1,4-oxazin-3-one, and 29.3 g of isobutyl nitrite were caused to react sequentially in 800 ml of anhydrous tetrahydrofuran in a manner similar to that described in Example III. Following a similar workup, 44.7 g of a thick oil were obtained which could not be induced to crystallize. Part (10 grams) was chromatographed on silica gel eluting the product band (3.0 grams) with acetone after unchanged starting material (5.4 grams) had been eluted with isopropyl ether/acetone mixtures. Trituration of the product fraction with ethyl acetate afforded pure oxime product, 2.9 g, mp. 168.5°–170.0°, equivalent to a total yield (in 44.7 g of crude product) of 13.0 grams.

Anal: Calc'd for $C_7H_{12}N_2O_3$: C, 48.83; H, 7.02; N, 16.27; Found: C, 47.11; H, 7.01; N, 15.76.

EXAMPLE V

Preparation of 2-Methylcarbamoyloximino-4-methyltetrahydro 1,4-oxazin-3-one

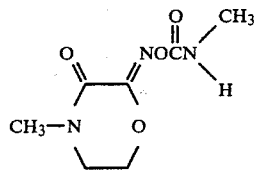

To a slurry of 2.9 grams of 2-oximino-4-methyltetrahydro-1,4-oxazin-3-one and 25 microliters of triethylamine in 150 ml of acetonitrile magnetically stirred in a 300 ml pressure bottle was added, in portions at the rate 0.5 ml/15 mins., 10 ml of a solution of 3.2 ml of methylisocyanate in 16.8 ml of acetonitrile. After stirring the resultant solution for 72 hours, the solution was treated with carbon black, filtered, and the solvent evaporated. Trituration with a mixture of ethyl acetate and isopropyl ether afforded 3.9 grams of the product, mp 177°–9°.

Anal: Calc'd for $C_7H_{11}N_3O_4 \cdot \frac{1}{2}H_2O$: C, 40.00; H, 5.75; N, 19.99; Found: C, 39.99; H, 5.61; N, 19.77.

EXAMPLE VI

Preparation of 2-[N-Trichloromethanesulfenyl-N-methylcarbamoyloximino]-4-methyltetrahydro-1,4-oxazin-3-one

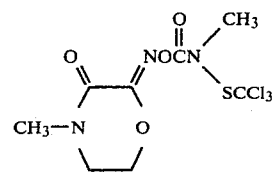

A quantity of 2.53 g. of 2-oximino-4-methyltetrahydro-1,4-thiazin-3-one and 4.9 g of N-methyl-N-trichloromethansulfenylcarbamoyl fluoride (West German Pat. No. 1,297,095; Farbenfabriken Bayer, A. G., June 12, 1969) and 1.5 ml of triethylamine in 175 ml of tetrahydrofuran were caused to react in a manner similar to that described for N-trichloromethanesulfenyl-N-methylcarbamates in Netherlands Pat. No. 7,404,474, Union Carbide Corporation, July 10, 1974. Conventional workup and recrystallization from acetone/isopropyl ether afforded 4.0 g of the product, mp 166°–168°.

Anal: Calc'd for $C_8H_{10}Cl_3N_3O_4S$: C, 27.41; H, 2.87; N, 11.98; Found: C, 27.41; H, 2.75; N, 11.92.

EXAMPLE VII

Preparation of 2-[N-Trichloromethanesulfenyl-N-methyl/carbamoyloximino]-4,5,5-trimethyltetrahydro-1,4-oxazin-3-one

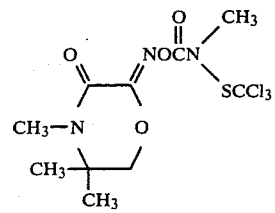

In a manner similar to that described in Example VI, 1.5 g of 2-oximino-4,5,5-trimethyltetrahydro-1,4-oxazin-3-one, 2.2 g of N-methyl-N-trichloromethanesulfenylcarbamoyl fluoride and 1.40 ml of triethylene were caused to react in 350 ml of tetrahydrofuran. Conventional workup and recrystallization from acetone/isopropyl ether afforded 1.46 g of product, mp 165°–166°.

Anal: Calc'd for $C_{10}H_{14}Cl_3N_3O_4S$: C, 31.72; H, 3.73; N, 11.09; Found: C, 31.47; H, 3.55; N, 11.12.

EXAMPLE VIII

Preparation of 2-Methylcarbamoyloximino-4,-6-dimethyltetrahydro-1,4-oxazin-3-one

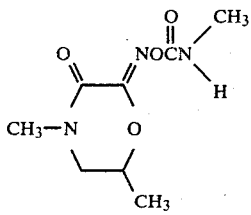

In a manner similar to that described in Example V, 0.5 grams of 2-oximino-4,6-dimethyltetrahydro-1,4-oxazin-3-one, 10 ml of triethylamine and 0.25 ml of methyl isocyanate were caused to react in acetonitrile. Conventional workup and trituration with isopropyl ether/ethyl acetate afforded 0.650 grams of 2-methylcarbamoyloximino-4,6-dimethyltetrahydro-1,4-oxazin-3-one, mp. 170°–173°.

Anal: Calc'd for $C_8H_{13}N_3O_4$: C, 44.65; H, 6.09; N, 19.53; Found: C, 43.73; H, 5.64; N, 19.07.

The following compounds are representative of other compounds that are within the scope of this invention which can be prepared according to this invention by selecting appropriate starting materials for use in the procedures described above:

4,5-Dimethyl-2-(N,N-dimethylcarbamoyloximino)tetrahydro-1,4-oxazin-3-one
4-Propyl-2-butylcarbamoyloximino-tetrahydro-1,4-oxazin-3-one
4,6-Dimethyl-2-(n-butylcarbamoyloximino)tetrahydro-1,4-oxazin-3-one
4-Methyl-2-[N-(t-butylthiosulfenyl)-N-methylcarbamoyloximino]tetrahydro-1,4-oxazin-3-one.
4-Methyl-2-[N-(4-t-butylphenylthiosulfenyl)-N-methylcarbamoyloximino]tetrahydro-1,4-oxazin-3-one
4-Methyl-2-(N-allylcarbamoyloximino)tetrahydro-1,4-oxazin-3-one
4-Methyl-2-propargylcarbamoyloximino-tetrahydro-1,4-oxazin-3-one
4,5,6-Trimethyl-2-[N-(4-cyanophenylthiosulfenyl)-N-methyl carbamoyloximino]tetrahydro-1,4-oxazin-3-one
4-Cyclohexyl-2-[N-(4-methoxyphenylsulfenyl)-N-methylcarbamoyloximino]tetrahydro-1,4-oxazin-3-one
4-Allyl-2-[N-(4-tert-butylphenylsulfenyl)-N-methylcarbamoyloximino]tetrahydro-1,4-oxazin-3-one
4-Cyclopentanyl-2-(N-methylcarbamoyloximino)tetrahydro-1,4-oxazin-3-one
4-(2-Methoxyethyl)-2-(N-methylcarbamoyloximino)tetrahydro-1,4-oxazin-3-one
4-Methyl-2-(N-trifluoromethanesulfenyl-N-methylcarbamoyloximino)tetrahydro-1,4-oxazin-3-one
4-Methyl-2-[N-(2,4-dichlorophenylsulfenyl)-N-methylcarbamoyloximino]tetrahydro-1,4-oxazin-3-one
4-Methyl-2-(N-phenylthiosulfenyl-N-methylcarbamoyloximino) tetrahydro-1,4-oxazin-3-one
2,3-Dimethyl-5-(N-methylcarbamoyloximino)-1,3-oxazolidin-4-one
2-(N-Propylcarbamoyloximino)tetrahydro-1,4-oxazin-3-one
4-Propenyl-2-(N-methylcarbamoyloximino)-tetrahydro-1,4-oxazin-3-one
4-Hexyl-2-(N-methylcarbamoyloximino)-tetrahydro-1,4-oxazin-3-one
4-Isopropyl-2-(N-methylcarbamoyloximino)tetrahydro-1,4-oxazin-3-one
4-Cyclopropyl-2-(N-methylcarbamoyloximino)tetrahydro-1,4-oxazin-3-one
4,5,5,6,6-Pentamethyl-2-(N-methylcarbamoyloximino)-tetrahydro-1,4-oxazin-3-one
4-(2-Hexenyl)-2-[N-hexylthio-N-ethylcarbamoyloximino]-1,4-oxazin-3-one
4-Methyl-2-[N-hexylthiosulfenyl-N-methylcarbamoyloximino]-1,4-oxazin-3-one
4-Phenyl-2-[N-hexanoyl-N-methylcarbamoyloximino]-1,4-oxazin-3-one.
4-Methyl-2-(N-acetyl-N-methylcarbamoyloximino)tetrahydro-1,4-oxazin-3-one
4-Ethyl-2-(carbamoyloximino)tetrahydro-1,4-oxazin-3-one
4-Methyl-2-(N-hexyl-N-methylcarbamoyloximino)tetrahydro-1,4-oxazin-3-one Suspensions of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. The test procedures were as follows:

Bean Aphid Foliage Spray Test

Adults and nymphal stages of the bean aphid (*Aphis fabae* Scop.) reared on potted dwarf nasturtium plants at 65°–70° F. and 50–70 percent relative humidity, constituted the test insects. For testing purposes, the number of aphids per pot was standardized to 100–150 by trimming plants containing excess aphids.

The test compounds were formulated by diluting the stock suspension with water to give a suspension containing 500 parts of test compound per million parts of final formulation.

The potted plants (one pot per compound tested) infested with 100–150 aphids, were placed on a revolving turntable and sprayed with 100–110 milliliters of test compound formulation by use of a DeVilbiss spray gun set at 40 psig. air pressure. This application, which lasted 25 seconds, was sufficient to wet the plants to run-off. As a control, 100–110 milliliters of a water-acetone-emulsifier solution containing no test compound were also sprayed on infested plants. After spraying, the pots were placed on their sides on a sheet of white standard mimeograph paper which had been previously ruled to facilitate counting. Temperature and humidity in the test room during the 24 hour holding period were 65°–70° F. and 50–70 percent, respectively. Aphids which fell onto the paper and were unable to remain standing after being uprighted were considered dead. Aphids remaining on the plants were observed closely for movement and those which were unable to move the length of the body upon stimulation by prodding were considered dead. Percent mortality was recorded for various concentration levels.

Southern Armyworm Leaf Spray Test

Larvae of the southern armyworm (*Prodenia eridania, (Cram.)*), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for three days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (*Epilachna varivestis, Muls.*), reared on Tendergreen bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 10 psig air pressure. This application, which lasted 25 seconds, was sufficient to wet plants to run-off. As a control, 100-110 milliliters of a water-acetone-emulsifier solution containing no test compound were also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F. for three days. Although the larvae could easily consume the leaf within 24 to 48 hours, no more food was added. Larvae which were unable to move the length of the body, even upon stimulation, were considered dead.

Fly Bait Test

Four to six day old adult house flies (*Musca domestica, L.*), reared according to the specifications of the Chemical Specialities Manufacturing Association (Blue Book, McNair-Dorland Co., N.Y. 1954; pages 243-244, 261) under controlled conditions of 80°±5° F. and 50±5 percent relative humidity, were the test insects. The flies were immobilized by anesthetizing with carbon dioxide and twenty five immobilized individuals, males and females, were transferred to a cage consisting of a standard food strainer above five inches in diameter which was inverted over a wrapping-paper-covered surface. The test compounds were formulated by diluting the stock suspension with a 10 percent (by weight) sugar solution to give a suspension containing 500 parts of test compound per million parts of final formulation, by weight. Ten milliliters of the test formulation were added to a soufflé cup containing a one-inch square of an absorbent cotton pad. This bait cup was introduced and centered on the blotting paper under the food strainer prior to admitting the anesthetized flies. The caged flies were allowed to feed on the bait for twenty four hours, at a temperature of 80°±5° F. and the relative humidity of 50±5 percent. Flies which showed no sign of movement on prodding were considered dead.

Mite Foliage Spray Test

Adults and nymphal stages of the two-spotted mite (*Tetranychus urticae Koch*), reared on Tendergreen bean plants at 80±5 percent relative humidity, were the test organisms. Infested leaves from a stock culture were placed on the primary leaves of two bean plants six to eight inches in height, growing in a two-and-a-half inch clay pot. 150-200 Mites, a sufficient number for testing, transferred from the excised leaves to the fresh plants in a period of twenty four hours. Following the twenty four hour transfer period, the excised leaves were removed from the infested plants. The test compounds were formulated by diluting the stock suspension with water to give a suspension containing 500 parts of test compound per million parts of final formulation. The potted plants (one pot per compound) were placed on a revolving turntable and sprayed with 100-110 milliliters of test compound formulation by use of a DeVilbiss spray gun set at 40 psig. air pressure. This application, which lasted 25 seconds, was sufficient to wet the plants to run-off. As a control, 100-110 milliliters of a water solution containing acetone and emulsifier in the same concentrations as the test compound formulation, but containing no test compound, were also sprayed on infested plants. The sprayed plants were held at 80±5 percent relative humidity for six days, after which a mortality count of motile forms was made. Microscopic examination for motile forms was made on the leaves of the test plants. Any individual which was capable of locomotion upon prodding was considered living.

Nematocide Test

The test organism used was the infective migratory larvae of the root-knot nematode, *Meloidogyne incognita* var. *acrita,* reared in the greenhouse on roots of cucumber plants. Infected plants were removed from the culture, and the roots are chopped very finely. A small amount of this inoculum was added to a pint jar containing approximately 180 cc. of soil. The jars were capped and incubated for one week at room temperature. During this period eggs of the nematode were hatched, and the larval forms migrated into the soil.

Ten ml. of the test formulation were added to each of the two jars for each dosage tested. Following the addition of chemical, the jars were capped, and the contents thoroughly mixed on a ball mill for 5 minutes.

The test compounds were formulated by a standard procedure of solution in acetone addition of an emulsifier, and dilution with water. Primary screening tests were conducted at 3.33 m.g. of the test compound per jar.

The jars were left capped at room temperature for a period of 48 hours, and the contents then transferred to 3 inch pots. Subsequently, the pots were seeded to cucumber as an indicator crop and placed in the greenhouse where they were cared for in the normal fashion for approximately 3 weeks.

The cucumber plants were then taken from the pots, the soil removed from the roots, and the amount of galling visually rated.

The results of these tests are set forth in Table I below. In these tests the pesticidal activity of the compounds against aphid, mite, Southern Armyworm, Mexican Bean Beetle, nematodes and house fly was rated as follows:

A = excellent control
B = partial control
C = no control
Dashes indicate no test conducted.

Certain of these compositions were also evaluated to determine their peroral toxicity to mammals. The animal selected for this experiment was the art. The test results obtained are expressed in terms of the number of milligrams of compositions per kilogram of weight of the animal required to achieve a mortality rate of 50 percent ($LD_{50}$).

The results of all of these tests are set forth in Table I below:

TABLE I

| Structure | m.p.°C. | Biological Activity | | | | | | Acute oral Rat mg/kg |
|---|---|---|---|---|---|---|---|---|
| | | Aphid | Mite | Southern Army Worm | Bean Beetle | Housefly | Nematode | |
| (structure 1) | 177–179° | A | A | A | A | A | A | 343.0 |
| (structure 2) | 166–168° | A | B | C | A | A | A | — |
| (structure 3) | 124–125° | A | A | C | A | A | A | 126.0 |
| (structure 4) | 165–166.5° | A | A | C | B | A | — | 794.0 |
| (structure 5) | 123.5–124.5° | A | A | A | C | A | C | 23.8 |
| (structure 6) | 144–146° | A | A | C | A | A | A | — |

TABLE I-continued

| Structure | m.p.°C. | Aphid | Mite | Southern Army Worm | Bean Beetle | Housefly | Nematode | Acute oral Rat mg/kg |
|---|---|---|---|---|---|---|---|---|
| (morpholine with CH₃CH₂–N, attached to C=NOCN(CH₃)H with C=O) | 88–89° | A | A | C | C | A | C | — |
| (morpholine with (CH₃)₂CH–N, attached to C=NOCN(CH₃)H with C=O) | — | A | C | C | C | A | — | — |
| (2-methylmorpholine with CH₃–N, attached to C=NOCN(CH₃)H with C=O) | 170–173° | A | A | A | A | A | A | — |
| (morpholine with CH₃CH₂CH₂N, attached to C=NOCN(CH₃)H with C=O) | 70–79° | A | A | A | B | A | C | |

The compounds contemplated in this invention may be applied as insecticides, miticides and nematocides according to methods known to those skilled in the art. Pesticidal compositions containing the compounds as the active toxicant will usually comprise a carrier and-/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistant with the desired dispersion of the toxicant in the spray so that rain does not re-emulsify the toxicant after it is applied to the plant and wash it off the plant. Nonionic, anionic, amphoteric or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentrate will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects, nematodes and mites upon plants or other material to which the pesticides are applied, and they have relatively high residual toxicity. With respect to plants, they have a high margin of safety in that when used in sufficient amount to kill or repel the insects, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are now compatible with substantially any other constituents of the spray schedule, and they may be used in the soil, upon the seeds, or the roots of plants without injuring either the seeds or roots of plants. They may also be used in combination with other pesticidally active compositions.

What is claimed is:
1. A compound of the formula:

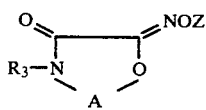

wherein:

Z is hydrogen;

R₃ is hydrogen, alkyl, cycloalkyl, alkoxyalkyl or phenyl;

A is ethylene either unsubstituted or substituted with one or more alkyl;

wherein the alkoxyalkyl, alkyl or cycloalkyl moieties individually may not contain more than 6 carbons.

2. A compound according to claim 1 wherein R₃ is hydrogen or alkyl.

3. A compound according to claim 1 wherein A is unsubstituted ethylene.

4. A compound according to claim 1 wherein A is ethylene substituted with one or more methyl or ethyl substituents in any combination.

5. 2-Oximino-4,6-dimethyl-tetrahydro-1,4-oxazin-3-one.

6. 2-Oximino-4,5,5-trimethyltetrahydro-1,4-oxazin-3-one.

* * * * *